United States Patent [19]
Karami et al.

[11] Patent Number: 5,167,613
[45] Date of Patent: Dec. 1, 1992

[54] COMPOSITE VENTED WOUND DRESSING

[75] Inventors: Hamzeh Karami, Mansfield; Ronald F. Vitaris, Worcester, both of Mass.

[73] Assignee: The Kendall Company, Mansfield, Mass.

[21] Appl. No.: 856,415

[22] Filed: Mar. 23, 1992

[51] Int. Cl.⁵ .................. A61F 13/00; A61F 15/00
[52] U.S. Cl. ........................... 602/42; 602/47; 602/57; 602/58
[58] Field of Search ............ 602/42, 47, 57, 58; 128/888

[56] References Cited

U.S. PATENT DOCUMENTS

| | | | |
|---|---|---|---|
| 4,231,357 | 11/1980 | Hessner | 602/47 |
| 4,541,426 | 9/1985 | Webster | 602/47 |
| 4,614,183 | 9/1986 | McCracken et al. | 602/57 |
| 4,909,243 | 3/1990 | Frank et al. | 602/58 |
| 5,086,763 | 2/1992 | Hathman | 602/42 |
| 5,086,764 | 2/1992 | Gilman | 602/54 |

FOREIGN PATENT DOCUMENTS 1914096  10/1970  Fed. Rep. of Germany ...... 128/888

*Primary Examiner*—Paul Prebilic
*Attorney, Agent, or Firm*—Al Isaacs

[57] ABSTRACT

Disclosed is a wound dressing consisting of a primary dressing for placement on the skin to cover a wound and an overlying secondary dressing containing an absorbent pad for receiving and retaining wound fluids diffusing thereto from the underlying wound and primary dressing, the secondary dressing being releasably secured to the primary dressing around their common periphery by a pressure-sensitive adhesive, at least the peripheral outer surface of the primary dressing having a release coating whereby to facilitate removal and replacement of the secondary dressing without disturbing the primary dressing or the healing wound therebeneath.

5 Claims, 3 Drawing Sheets

COMPOSITE VENTED WOUND DRESSING

BACKGROUND OF THE INVENTION

It is most desirable in wound treatment to provide an adhesive dressing which will maintain the desired moist environment promoting healing while preventing scab formation; and also permitting removal of wound fluid which can build up to a pressure bubble beneath the dressing, thereby undermining the adhesive seal to the skin and thus increasing the possibility of the wound being contacted by ambient contaminants, including, of course, microorganisms which can cause infection.

Seemingly, these two objectives are often at cross-purposes so that one of the two desired objectives is accomplished to the detriment of the other.

Yet, dressings fulfilling both objectives are heretofore disclosed in the art.

By way of illustration, reference is made to U.S. Pat. No. 4,541,426 issued to Webster whose discussion of the prior art as background to the invention is additionally worth mentioning.

As stated in Col. 1 of the patent:

It has long been a recognized problem that dressings are inclined to suffer from either or both the disadvantages that they sometimes tend to float away from a wound or else they sometimes tend to adhere to the wound surface.

The first of these disadvantages generally occurs when the wound is one that produces large volumes of exudate. Generally the method of overcoming this problem is to provide the dressing with holes so that the exudate can escape and the dressing remain in contact with the wound. Certain attempts to achieve this end are disclosed in U.K. Pat. Nos. 778813, 1298011, 1408345 and U.D. Patent Application Nos. 2061732 and 2074029. One successful dressing is Melolin (Trad make. available from T. H. Smith and Nephew Ltd., Hull, U.K.) which comprises a perforated synthetic polymer film and anabsorent cellulosic pad. The perforated film is placed next to the exuding wound, the exudate passes through the perforations and is absorbed by the pad. A more recent suggestion has been to use a perforated polytetrafluoroethylene film in an effort to minimise the risk of any adherency of the dressing to the wound.

Alternatively dressings have ben suggested which comprise a thin hydrophobic film laminated to a fibrous absorbent layer. The film contains a number of apertures in the form of slits. Such dressings are described in, for example, British Pat. Nos. 815,121 and 1,163,452 and U.S. Pat. No. 3,602,220. However dressings of that type have not been found to be satisfactory because either the slits do not open or do not open wide enough to allow passage of exudate through the film to the absorbent.

The second of the aforementioned disadvantages generally occurs when the wound has dried out due to lack of production of exudate. Generally the method of overcoming this problem is to provide the dressing with a continuous layer which retards the rate of loss of water. One effective method of achieving this end is described in British Pat. No. 1280631.

However none of the known methods are free of disadvantages since what may be an excellent dressing for one kind of wound will be unsuitable for many other wounds since wounds differ greatly in their output of exudate. It has now been realised that, none only is there a need of a dressing which is suitable for use on a number of different wound types, there is also a need for a dressing which can better cope with the variation in rate of exudate production from a given wound. A dressing has now been discovered which allows passage of a greater amount of exudate from a wound which produces greater amounts of exudate and which aids in allowing the wound to remain a moist wound when it produces only smaller amounts of exudate so that it does not float away from the moist surface and has a reduced tendency to adhere to the wound. The new dressing has been found to aid in the re-epithelialisation of the wound.

Accordingly, the patented invention is said to provide a dressing comprising a conformable film with apertures therethrough characterized in that the film comprises a first layer laminated to a second layer, the first layer comprising a material which swells when in contact with water and the second layer comprising a material which when in contact with water does not swell or swells less than the first layer. According to the patentee the apertures are enlarged when in use on a wet surface and otherwise not enlarged, the enlarged openings permitting passage of water, e.g. wound exudate, the apertures when not enlarged preventing the wound from drying out; i.e. providing a moist environment.

U.S. Pat. No. 5,086,764 issued to Thomas H. Gilman Feb. 11, 1992 and assigned to The Kendall Company, assignee of the present invention describes and claims a composite dressing comprising a base sheet for placement on the skin surrounding a wound, the base sheet having an adhesive on a front surface thereof for securing the dressing to the skin, the base sheet having an opening extending therethrough for venting wound exudate, an absorbent layer separate from the base sheet and located on a back surface of the base sheet, the absorbent layer covering the opening to permit replacement of the absorbent layer without removal of the base sheet from the patient's skin, and a back sheet covering the absorbent layer, the back sheet being releasably secured to the base sheet.

Another embodiment of a composite vented dressing permitting removal of wound fluids while maintaining a moist environment is described and claimed in copending application of Thomas H. Gilman, Ser. No. 337,591 filed Apr. 13, 1989 and now U.S. Pat. No. 5,106,362, also assigned to the common assignee.

As disclosed therein, the dressing will comprise: a base sheet for contacting the skin, the base sheet having an opening for placement over a wound and adhesive means for securing the base sheet to the skin; and vent means for providing controlled leakage of fluid along a path from the wound through the opening of the base sheet, the vent means comprising cover means covering the opening, the cover means permitting passage of wound fluid therethrough while reducing evaporation through the opening and thereby helping to insure a moist environment when excess wound fluid is removed from the wound.

The dressing may have an absorbent fabric layer secured around its periphery to the back surface of the base sheet.

U.S. Pat. No. 5,056,510 of Thomas H. Gilman describes and claims a composite wound dressing comprising a base sheet having at least one opening adapted for placement over a wound, vent means for providing controlled leakage of wound fluid along a path from the wound through each of the openings of the base sheet, the vent means permitting passage of wound fluid therethrough while reducing evaporation through each opening to help insure a moist environment when excess wound fluid is removed from the wound, a cover element secured to the dressing over the base sheet and vent means, the cover element defining a chamber into which wound fluids leaking through the vent means can wick or diffuse, and a fabric reservoir for receiving and retaining wound fluids within the chamber.

Finally, a particularly efficacious composite vented dressing for removing excess wound fluids while maintaining a moist environment conducive to wound healing is disclosed in the copending application of Hamzeh Karami and Thomas H. Gilman, Ser. No. 738,983 filed Jul. 29, 1991 and also assigned to the common assignee.

As is described and claimed therein, the vented wound dressing comprises a thin conformable sheet material, at least a portion of which is adapted for placement over a wound having a pressure-sensitive adhesive layer on one surface thereof, the adhesive layer being applied to provide repeating spaced areas free of adhesive. Preferably the non-adhesive areas are arranged in a geometric pattern. In any case, while the non-adhesive areas are shown for purposes of illustration as being generally circular, the configuration is not critical and they may be of any desired shape, e.g. oval, rectangular, arcuate, etc.

At least a portion of the repeating areas of no adhesive have slits extending through the thickness thereof to permit transfer of wound fluids through the sheet material unimpeded by the presence of adhesive material which can clog the slits and thereby inhibit fluid transfer therethrough.

As is further described and claimed therein, the aforementioned vented dressing will additionally contain thereover an absorbent pad or the like providing a reservoir for receiving and retaining wound fluids diffusing through the slits in the primary dressing. Most preferably, a cover sheet providing a bacterial barrier is situated over the reservoir.

Common to all the composite dressings described above and assigned to The Kendall Company, assignee of this invention, is the concept of providing a vented dressing for placement on the skin and covering the wound, hereinafter referred to as the "primary dressing" over which is releasably secured by a pressure-sensitive adhesive what is hereinafter referred to as the "secondary dressing" and which includes a reservoir containing an absorbent fabric and which has an outer cover. As disclosed in each of these cases, the primary dressing permits diffusion of wound exudate to the overlying secondary dressing while maintaining a moist environment. Also, as disclosed in each of these cases, the secondary dressing is intended to receive and to retain wound exudate diffusing thereto through the underlying primary dressing.

In the composite primary/secondary dressings described above it is most desirable for the secondary dressing to be removable from the primary dressing in order to observe the progress in wound healing and/or to replace the secondary dressing with a fresh new one on an as needed basis when the old one becomes or is about to become saturated with wound exudate.

More particularly, it is most desirable that the secondary dressing be readily removable without pulling or tugging so as to dislodge the primary dressing or irritate the healing wound.

It has been found, however, that the adhesive bond between the two dressings for securing the secondary dressing over the primary dressing does not permit separation for removing the secondary dressing as easily as desired.

BRIEF DESCRIPTION OF THE INVENTION

Stated simply, the task of this invention is to facilitate separation of primary and secondary dressings of the type disclosed in the aforementioned patents and copending applications while at the same time maintaining sufficient tackiness for the secondary dressing to adhere during its contemplated usage.

In accordance with this invention this task is solved in an elegant manner by providing a release coating around at least that portion of the outer surface of the primary dressing intended to be adhered to the secondary dressing, the release coating being sufficiently tight so that the respective dressings will remain together against the reasonable external forces expected to be encountered, e.g. movement, rubbing against bed garments, etc., when applied to cover a patient's wound.

DETAILED DESCRIPTION OF THE INVENTION

As was heretofore mentioned, the present invention is directed to composite dressings consisting of a primary dressing permitting venting excess wound fluids while maintaining a moist environment promoting wound healing in combination with a secondary dressing having an absorbent fabric reservoir for receiving and retaining wound fluids diffusing thereto from the primary dressing.

The nature and objects of the invention may best be understood by reference to the illustrative drawings directed to the preferred embodiments of this invention in combination with the following detailed description.

The preferred embodiment is directed to a vented dressing of the type disclosed in the aforementioned copending application, Ser. No. 738,983 wherein the primary dressing applied to cover the wound comprises a thin, conformable, liquid-impermeable, vapor-permeable sheet material having an adhesive coating on one surface thereof for adhering the dressing to the skin, the adhesive coating in the portion of the dressing for placement over the wound being applied so as to provide repeating areas containing no adhesive, areas of the sheet material where there is no adhesive having slits extending through the thickness thereof to permit venting of wound fluids therethrough.

Figure 1:
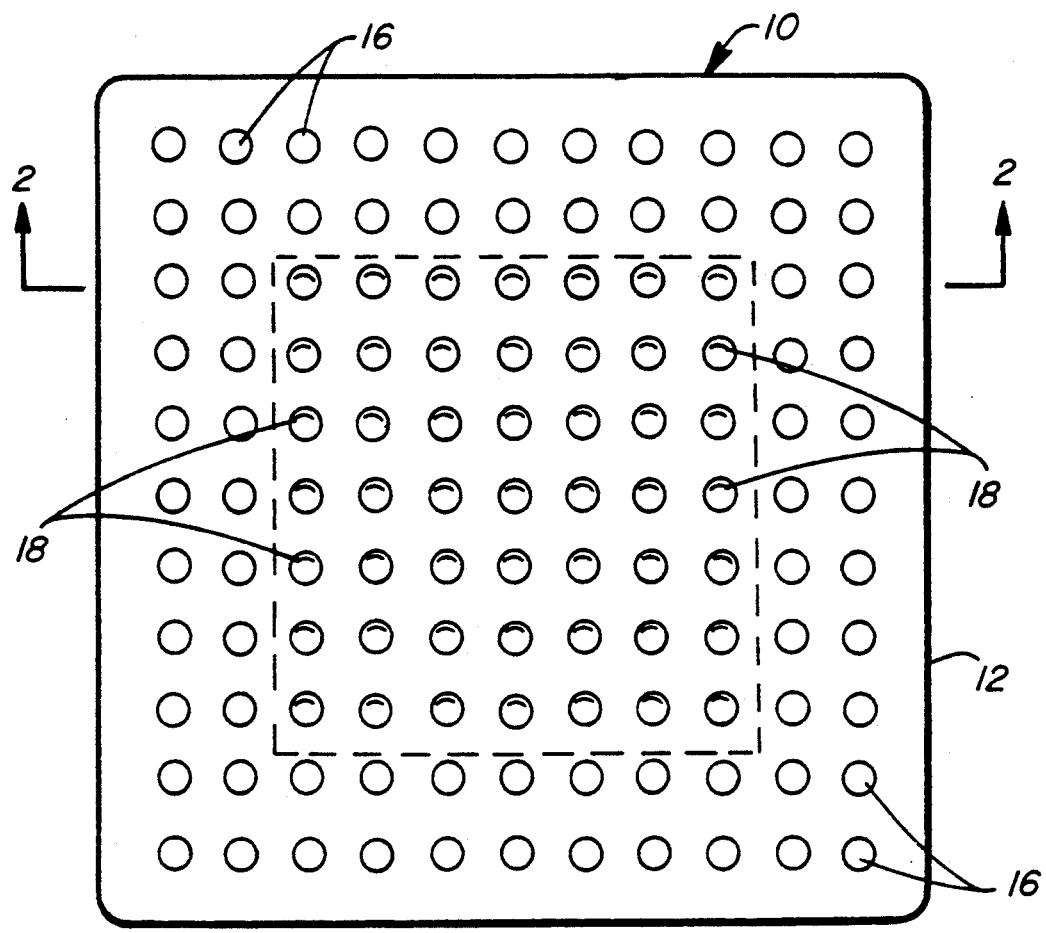
FIG. 1 is a bottom view of the primary dressing for placement on the wound.
Figure 2:
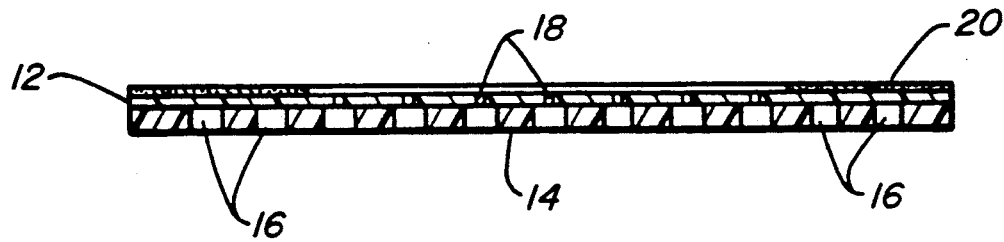
FIG. 2 is a sectional view of the primary dressing taken along lines 2—2 of FIG. 1.

With reference to FIGS. 1 and 2, the primary dressing 10 of this invention for placement on the wound in the preferred embodiment will comprise a thin conformable sheet material 12 having a per se known pressure-sensitive adhesive layer 14 on the underlying surface thereof, the adhesive layer being applied to provide repeating spaced areas 16 free of adhesive. Preferably the non-adhesive areas are arranged in a geometric pattern, e.g. in aligned rows, as shown in the drawing, or in staggered rows. In any case, while the non-adhesive areas 16 are shown for purposes of illustration as being generally circular, the configuration is not critical and they may be of any desired shape, e.g. oval, rectangular, arcuate, etc.

In the illustrative configuration shown in FIG. 1, the primary dressing is generally square and has a total of eleven adhesiveless areas in each row, both horizontal and vertical. The outer two horizontal and vertical rows are positioned in peripheral portions of the dressing intended for adherence to intact skin surrounding the wound areas. These peripheral portions define a generally centrally disposed portion consisting of non-adhesive areas 3–7 in each direction, which centrally disposed portion is intended to be placed directly over the wound.

Slits 18 are shown to be provided within each of the non-adhesive areas in the wound-covering portion. However, it is within the scope of this invention to provide slits in less than all of these non-adhesive areas, if found desirable to do so.

While the slits 18 are shown in FIG. 1 to be somewhat arcuate in shape, they may have other forms. For example, as shown in the aforementioned U.S. Pat. No. 4,541,426 of Webster, they may be linear or in the form of triangular flaps provided by slitting two sides of the triangle so that the flaps remain attached by the third side.

In the best mode contemplated by Applicants for carrying out the invention, attention is also focused on the task of preventing maceration which can occur to the healthy skin surrounding the wound due to the occlusion of water from transepidermal water loss under the overlying adhesive layer.

This task is solved by providing in this the peripheral portion of the primary dressing repeating areas of no adhesive which can be the same or different from those in the wound-covering portion of the dressing having slits to permit diffusion of exudate. However, since the passage of fluid from or into the dressing in these peripheral non-adhesive areas will not have slits so they will be characterized as being fluid-impermeable but vapor-transmissive.

In the illustrative drawing two rows of these non-adhesive areas 16 are shown to be slit-free.

The aforementioned concept of preventing maceration by providing in peripheral portions of the primary dressing repeating areas of no adhesive which are slit-free is described and claimed in Applicants' copending application, Ser. No. 856,413, filed concurrently.

While the primary dressing shown in FIGS. 1 and 2 is capable of utility by itself, the use to which it is particularly intended and the usage contemplated by this invention is in combination with a secondary dressing providing a reservoir for receiving wound fluids diffusing through the slits, which secondary dressing is releasably secured to the primary dressing by a pressure-sensitive adhesive (as will be discussed in more detail hereinafter) so as to be replaceable.

The secondary dressings envisioned in the practice of this invention will include an absorbent pad or other per se known equivalent absorbent material and an overlying cover sheet providing a bacterial barrier. The cover sheet will have a layer of pressure-sensitive adhesive around its periphery to releasably secure the secondary dressing to the primary dressing. Most preferably, at least a portion of the cover providing a bacterial barrier is also air-permeable to permit egress of air from the interstices or voids in the fabric reservoir to the ambient atmosphere. As will be appreciated, removal or displacement of entrained air within the fabric reservoir is necessary to free these interstices to act as a sponge for retention of wound fluids diffusing thereto, thereby appreciably increasing the capacity of the reservoir for receiving and retaining wound fluids.

Figure 3:
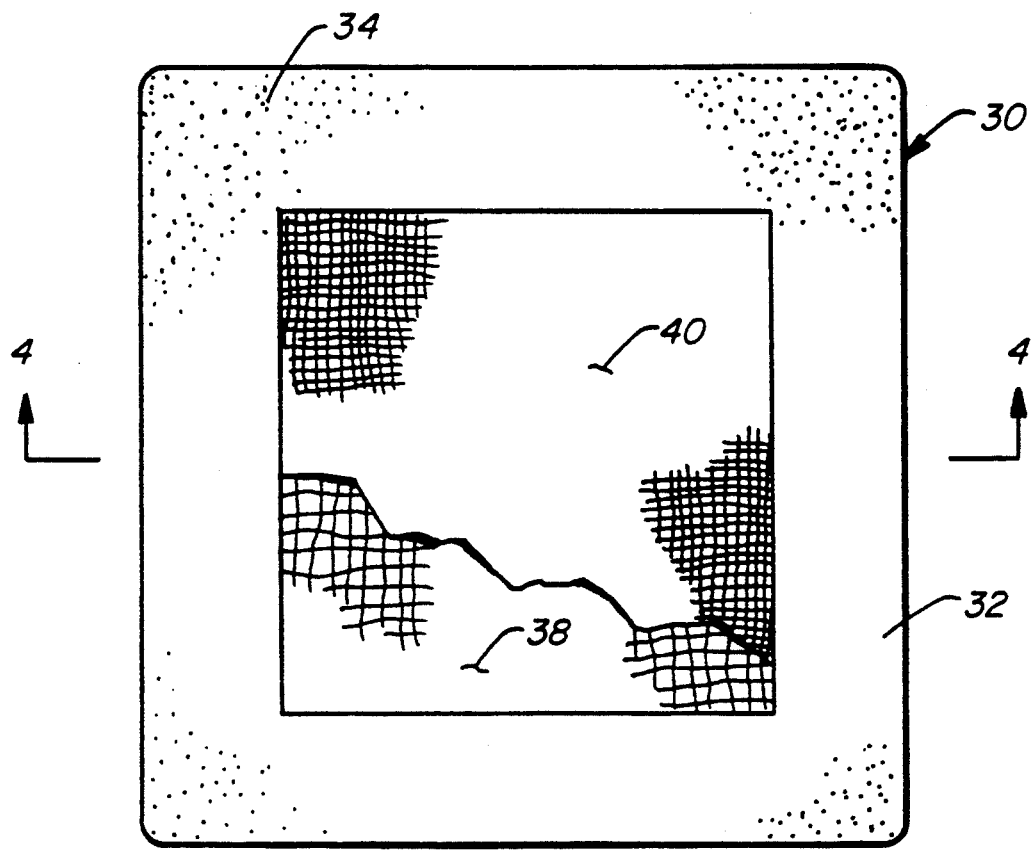
FIG. 3 is a perspective view of the preferred secondary dressing partially broken away to reveal the arrangement of elements.
Figure 4:
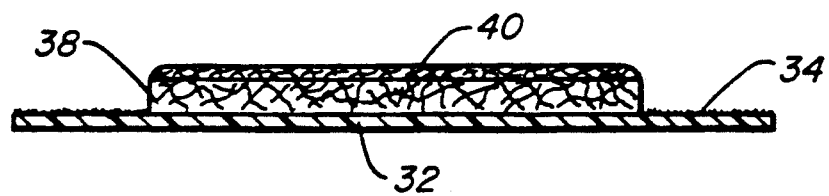
FIG. 4 is a sectional view taken along lines 4—4 of FIG. 3.

While the reservoir in the secondary dressing may comprise any of the fabric materials heretofore employed to retain exudate, e.g. cotton, gauze sponges, absorbent pads such as those customarily used for abdominal surgery, and the like, in the most preferred embodiment of this invention, it will consist of two separate but contiguous elements, namely a lower high density woven or non-woven fabric having optimum spreading or wicking characteristics, and an upper low density fabric having optimum absorption capacity. The concept of providing such a combination of high and low density fabrics in the secondary dressing is illustrated in FIGS. 3 and 4 and is described and claimed in the concurrently filed copending application, Ser. No. 856,414.

As best seen in FIG. 3, in the best mode contemplated for the practice of the instant invention, the secondary dressing 30 will comprise a high density fabric 40 and an overlying low density fabric 38 which together form a reservoir for receiving and retaining wound exudate. Preferably, the high density fabric will have a density of on the order of 0.1 to 0.2 gms/(cm)$^3$; while the low density fabric will have a density less than 0.1, e.g. on the order of 0.05 gms/(cm)$^3$. In a typical embodiment, the combination of fabrics 38 and 40 will provide a weight per surface area of on the order of 7 ounces/square yard, the ratio of low:high density by thickness being on the order of about 3:1 to about 5:1. The fabrics may be woven or non-woven materials, non-woven being preferred, and illustrative fibers include rayon, rayon/polyester or polyester/cotton blends, cotton, cellulosic materials, etc. Polymeric absorbent foams may also be used, if desired.

To maintain the integrity of the absorbent pad, e.g. during packaging and subsequent handling, fabrics 38, 40 may be adhered at their interface by suitable adhesive means.

With reference again to FIG. 3, the secondary dressing 30 will have a bacteria-impermeable, air-permeable cover sheet 32. As heretofore alluded to, in addition to the cover sheet providing a barrier to ingress of bacteria which could then pass through the slits 18 in sheet material 12 of the primary dressing and then to the underlying wound, the cover sheet 32 should additionally be air-permeable to permit egress of air from the interstices or voids in the fabric reservoir to the ambient atmosphere. Suitable materials for this purpose include polyurethane, a polyolefin such as polyethylene or polypropylene, "Saran" (trademark of Dow Chemical), a polyester such as polyethylene terephthalate, etc.

The cover sheet should also have a layer of pressure-sensitive adhesive 34 in its peripheral portions surrounding the fabric reservoir in order to seal the cover sheet in liquid—and bacteria—tight relationship around their common periphery so that exudate cannot escape through the edges of the dressing, nor can any external contaminants, including bacteria, enter into the dressing and then pass through the slits 18 to the underlying wound. To provide such a barrier, the adhesive layer 34 may, for example, be on the order of 10 mils thick.

Figure 5:
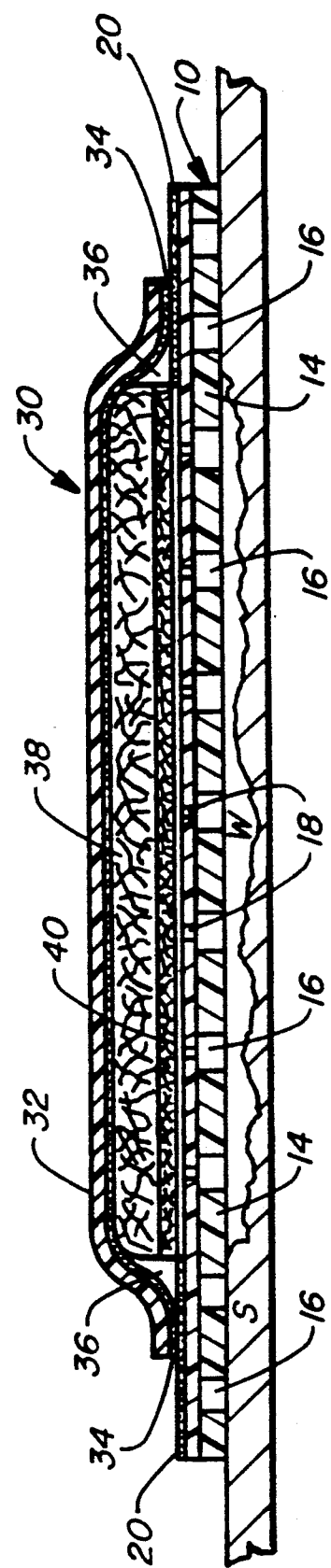
FIG. 5 is a sectional view showing the arrangement of the primary and secondary dressings in accordance with this invention.

While the cover sheet 32 may be a single sheet material, as shown in FIGS. 3–5, it is within the scope of this invention to provide a cover sheet of the type shown in U.S. Pat. Nos. 5,060,642 and 5,056,510 as well as the aforementioned copending application, Ser. No. 738,983, wherein the cover sheet is provided with one or more windows or openings each of which is covered by an air-permeable bacterial barrier sheet material, e.g. one of the per se know bacterial barrier air filters such as NUCLEOPORT, MILLIPORE, GELLMAN, etc.

Notwithstanding the bacterial barrier aspects of the cover sheet and the adhesive securing the cover sheet to the rear surface of the primary dressing, where found desirable to assure the proper bacteria-free environment, and antimicrobial agent such as chlorhexidine may be included in the absorbent pad reservoir. However, the use of such a reagent is not considered necessary in the practice of this invention.

As was previously mentioned, secondary dressings of this description are described and claimed in copending application Ser. No. 856,414 filed concurrently.

With reference now to FIG. 5, the relationship of the primary and secondary dressings in accordance with the invention may best be understood.

The primary dressing 10 is applied to cover the wound W with the peripheral portions free from slits 16 overlying the healthy intact skin S.

The secondary dressing 30 is then placed over the primary dressing with the absorbent pads 38, 40 squarely aligned with the edges of the outermost rows of non-adhesive areas having slits. This is readily observable by the clinician, thereby facilitating proper placement of the secondary dressing. When so positioned, the surface of cover sheet 32 bearing adhesive 24 will in accordance with the present invention, be superposed over and in direct contact with a release coating 20 on the outer surface of sheet 12 of the primary dressing (as will be described in detail hereinafter).

When so positioned, an elegant dressing is provided whereby wound exudate is permitted to diffuse through the slits in the primary dressing to the overlying secondary dressing where the exudate is wicked into the fabric reservoir and there absorbed. The slits permit the dressing to maintain a moist environment promoting wound healing while at the same time preventing reflux or "back diffusion" of exudate from the secondary dressing back into the wound. The adhesive 14 securing the primary dressing, outer cover 32, and the adhesive 34 securing the respective dressings together provide an environment for wound healing effectively precluding bacteria and any other external contaminants.

When it is desired to remove the secondary dressing either to observe the healing process or to replace it with a new one when the capacity of the reservoir to retain wound fluid is about to be reached, the release coating 20 renders separation easy without pulling on and/or displacing the primary dressing covering the wound.

It will be appreciated that in order to replace the secondary dressing, as herein contemplated, it should be readily separable from the primary dressing without causing discomfort to the patient or in any way moving or dislodging the primary dressing so as to cause insult to the underlying wound.

In accordance with the present invention, easy removal is facilitated by providing at least on the periphery of the non-adhesive-bearing surface of the sheet material 12 to be contacted by the adhesive coating on the secondary dressing a release coating 20, as best seen in FIG. 2.

The release coatings contemplated by this invention are characterized as providing a substrate to which adhesive layer 34 will adhere strong enough to maintain a bond retaining the two dressings together as a composite dressing while at the same time permitting ready separation when the clinician desires to examine the wound or to change the secondary dressing. A peel adhesion suitable for this purpose may, for example, be on the order of from about 0.18 to about 0.35 pound per two inches (lb/2") with a peel adhesion within the range of 0.25 to 0.30 being preferred.

Release coatings suitable for this purpose are well known in the art and per se comprise no part of this invention.

One class of particularly useful known release coatings may be formulated from solventless silicone coating compositions referred to in the art as "100% solids" compositions. By way of illustration, it may comprise a linear vinyl-functional polysiloxane polymer compounded with a reactive MQ resin in the presence of a platinum catalyst to form the desired cured release coating. As is well known in the literature, reactive MQ resins act as controlled release additives allowing adjustment of the release (i.e. the force in grams required to separate an adhesive from a substrate coated with a cured release coating) of silicone release compositions. MQ resins, which are well reported in the patent literature, are copolymers having $R_3SiO$ 0.5 and $SiO_2$ units in varying ratios, e.g. from about 0.25:1 to about 2:1, wherein each R maybe a lower alkyl, e.g. methyl.

The release coating 20 contemplated by this invention may, for example, comprise a monolayer of the foregoing description containing on the order of about 1.0 gram of solids per square meter of surface area.

In general, suitable materials for providing release coating 20 are well known in the art and their selection will be within the expected judgment of the skilled worker in the light of this description.

As heretofore mentioned, the preferred embodiment providing a primary dressing containing adhesiveless areas having slits therein to permit wound fluid to diffuse therethrough to an overlying reservoir, herein called a "secondary dressing" is described and claimed in copending application Ser. No. 738,983.

As stated in this copending application, the invention was predicated upon the initial discovery that an adhesive layer is essential to provide the requisite pressure build-up to open the slits. In accordance with the claimed invention, the adhesive-free areas containing the slits for removal of excess wound exudate are isolated by the adhesive coating forming a dam or barrier inhibiting lateral diffusion of the exudate so that it is instead directed upwardly through the slits provided in the dressing sheet. As further stated therein, for optimum effectiveness the ratio of surface area of the wound-covering portion which contains adhesive to the surface area in that portion which does not should be at least 1:1 i.e. at least 50% of the surface area of that portion should contain adhesive application.

As is further stated in this copending application "the non-adhesive areas in theory need not be any larger than slits to be provided therein. However, to provide optimum manufacturing tolerance for the slitting operating to be sure the slits do not at least in part inadvertently overlap into the adhesive area, it has been found that the non-adhesive areas should be at least on the order of about ⅛ inch wide in the directions of the slit. For example, if the non-adhesive areas are circular, they should have a ⅛ inch diameter; and if they are square the length and width should be on the order of ⅛ inch. In any case, one skilled in the art will understand that the minimal dimensions will depend primarily upon the preciseness of the manufacturing equipment to provide the slits accurately in the prescribed non-adhesive areas.

"In addition to permitting diffusion of wound exudate away from the wound and through the slits, it is essential that the wound dressings of this invention provide a barrier to evaporation of water (as distinguished from a barrier to removal of exudate) so as to keep the wound surface moist as excess exudate is removed."

"The benefits of maintaining a moist wound surface are of course well known and include faster reepithelization, less pain and better cosmetic results."

"In order to do so, in accordance with the present invention the size and number of slits in the dressing should be such as to provide a dressing of the type known in the art as a moist healing wound dressing." In order to do so in accordance with this invention the size and number of slits should be such as to maintain a moisture vapor permeability or transition rate for the dressing of no greater than 1500 grams/meter/24 hours at 37° C. and 50% relative humidity.

"By way of illustration, successful results have been obtained by providing 5–8 ⅛" diameter non-adhesive areas per square inch of surface area to obtain the preferred moist dressing."

"The slits will optimally extend across the width or diameter of the non-adhesive areas. With ⅛" diameter circular areas, excellent results have been obtained with cross slits across the diameter of the circle. Many other slit designs may also be employed. For example, equal success has been obtained with 3/64 inch radius half circle slits in ⅛ inch diameter areas."

"The vented dressing of this invention may be prepared in the following manner:"

(1) apply an adhesive layer of the desired thickness by calendaring, casting, etc. between two release sheets of differential affinity;

(2) punch holes of the desired configuration and spacing through the thickness of the resulting "sandwich";

(3) remove the release sheet of lesser affinity from the adhesive, leaving the other release sheet of greater affinity adhering to the opposed surface of the adhesive;

(4) apply the free adhesive surface to the surface of the desired elastomeric sheet;

(5) provide slits by cutting the sheet in areas where there is no adhesive, i.e. in those areas where holes had been punched through the adhesive "sandwich"; and (6) "thereafter replace the release sheet having the holes punched through it with a new one free from holes. . . ."

By way of recapitulation, the present invention is directed to composite primary/secondary dressings wherein the primary dressing for placement over the wound has vent means for removing excess wound fluids while providing a proper moist environment conducive to wound healing and the secondary dressing contains an absorptive fabric for receiving and retaining wound fluids diffusing thereto through the vent means in primary dressing. The composite dressing provides a barrier to external contaminants, including bacteria. A very significant technical advance in the wound treatment art is provided by the fact that the secondary dressing is removable and replaceable on an as needed basis without dislodging the primary dressing, causing any discomfort to the patient, or damage to the healing wound.

The essence of the present invention is providing the described monolayer release coating which facilitates separation of the secondary dressing from the primary one while at the same time permitting the secondary dressing to adhere so as to provide the desired composite wound dressing.

While the invention has been described in detail with reference to the primary dressings of Ser. No. 738,983 wherein repeating areas of no adhesive are provided with slits to vent the wound fluids, it is to be expressly understood that the invention is not limited thereto and is obviously applicable as well to other primary/secondary composite wound dressings including, but not limited to those mentioned in the BACKGROUND OF THE INVENTION.

The particular selection of materials which may be employed for the various components of the composite herein contemplated are per se known in the art and, accordingly, their selection may be considered to be a matter of individual choice or whim within the expected judgment of the skilled worker in the light of the foregoing description.

By way of illustration, sheet 12, which is flexible so as to be conformable to the contour of the body part to which it is to be applied, may be as thin as 0.5 mil or as thick as 5.0 mil, but is preferably on the order of 1.0 mil thick. Preferably, it is an elastomer which is characterized as being non-swellable or only slightly swellable. Materials useful for preparing slitted sheet 12 are well known in the art and will be readily suggested to those skilled in the art in the light of the foregoing description. For example, useful materials will include polyurethane, copolyesters such as "HYTREL", polyvinyl chlorides, polyolefins, etc.

The adhesive materials employed may likewise by any of the known so-called medical grade or hypoallergenic adhesives heretofore employed in securing dressings to the skin. Such known adhesives include the rubber-based, acrylic, vinyl ether and hydrocolloid pressure-sensitive adhesives. The adhesive may be applied to provide a layer of at least 1 mil thick, but preferably layers of adhesive at least 5 mils thick, e.g. on the order of 5–10 mils are contemplated.

The adhesive materials employed may likewise by any of the known so-called medical grade or hypoallergenic adhesives heretofore employed in securing dressings to the skin. Such known adhesives include the rubber-based, acrylic, vinyl ether and hydrocolloid pressure-sensitive adhesives. The adhesive may be applied to provide a layer of at least mil thick, but preferably layers of adhesive at least 5 mils thick, e.g. on the order of 5–10 mils are contemplated.

While not essential to the use of the composite dressings herein contemplated, most preferably sheet 12 will be sufficiently transparent so that the underlying wound can be seen by the clinician to observe the healing process without removing the dressing. Useful transparent sheet materials include those recited above.

It will be appreciated that various changes may be made without departing from the invention described in the foregoing specification and defined in the appended claims.

For example, where found desirable or expedient to do so, the outer edges of cover sheet 32 may be adhesive-free to assure that there be no oozing of adhesive on the skin beyond the overlying dressing.

It is also postulated that the adhesive 32 surrounding the pads 38, 30 may be deposited so as to provide repeating areas of no adhesive in order to increase the rate of moisture vapor transmission and thereby inhibit maceration the underlying healthy, intact skin surrounding the wound.

In the foregoing description, reference has been made throughout to applying the silicone release coating directly to the outer surface of the sheet material of the primary dressing. In lieu thereof, in a less preferred embodiment contemplated by this invention, the release coating may be contained on a frame-like separate sheet material which is laminated to the surface of the primary dressing sheet material around the periphery thereof, e.g. by heat sealing by means of a suitable adhesive, etc.

From the foregoing description it will therefore be seen that the present invention permits ready separation of the secondary dressing from the primary dressing while at the same time providing means for retaining the two dressings together so as to prevent accidental or unwanted separation during normal contemplated usage.

Since certain changes may be made without departing from the scope of the invention herein contemplated, it is intended that the foregoing description and accompanying drawing be taken as being illustrative and not in a limited sense.

What is claimed is:

1. In a composite vented wound dressing comprising:
   (a) a primary dressing for placement over a wound, the primary dressing having a thin, conformable sheet material having a pressure-sensitive adhesive coating on one surface thereof for adhering the dressing to the skin and vent means for diffusing wound fluid through the sheet material; and
   (b) a secondary dressing in superposition with non-adhesive-bearing surface of the sheet material of the primary dressing, the secondary dressing having a reservoir for receiving and retaining wound fluid diffusing thereto through the vent means in the primary dressing therebeneath and a cove sheet covering the reservoir, the cover sheet having a layer of pressure-sensitive adhesive at least around the periphery of the surface in juxtaposition with the superposed sheet material of the primary dressing to releasably seal the secondary dressing to the surface of the primary dressing, the secondary dressing thereby being removable and replaceable as needed without disturbing the primary dressing covering the wound;

the improvement wherein the non-adhesive-bearing surface of the sheet material of the primary reference in contact with the pressure-sensitive adhesive coating on the cover of the secondary dressing to releasably secure the respective dressings together contains a release coating to facilitate removal of the secondary dressing, the release coating being adapted to retain the dressings together so a to prevent accidental or unwanted separation while at the same time permitting ready separation of the secondary dressing from the primary dressing.

2. A dressing as defined in claim 1 wherein the release coating comprises a solventless silicone release coating composition.

3. A dressing as defined in claim 2 wherein the release coating is applied to the sheet material of the primary dressing as a monolayer.

4. A dressing as defined in claim 1 wherein the release coating is characterized by having a peel adhesion on the order of from about 0.18 to about 0.35 pound per two inches.

5. A composite wound dressing as defined in claim 1 wherein the primary dressing comprises a thin conformable sheet material, at least a portion of which is adapted for placement over a wound and having a pressure-sensitive adhesive layer on one surface thereof for adhering the dressing to the body, the adhesive layer being applied to provide repeating spaced areas free of adhesive, at least a portion of the repeating areas of no adhesive having slits extending through the thickness thereof to permit transfer of wound fluids through the sheet mateial unimpeded by the presence of adhesive material which can clog the slits and thereby inhibit fluid transfer therethrough.

* * * * *